United States Patent [19]

Härdtl et al.

[11] Patent Number: 5,792,666

[45] Date of Patent: Aug. 11, 1998

[54] OXYGEN SENSOR BASED ON NON-DOPED CUPRATE

[76] Inventors: Karl-Heinz Härdtl, Prof.-Eichmann-Strasse 27, D-76767 Hagenbach; Rainer Blase, Hardeckstrasse 14a, D-76185 Karlsruhe; Ulrich Schönauer, Sternbergstrasse 1, D-76131 Karlsruhe, all of Germany

[21] Appl. No.: 448,599

[22] PCT Filed: Jul. 4, 1994

[86] PCT No.: PCT/EP94/02185

§ 371 Date: Jan. 29, 1996

§ 102(e) Date: Jan. 29, 1996

[87] PCT Pub. No.: WO95/04270

PCT Pub. Date: Feb. 9, 1995

[30] Foreign Application Priority Data

Jul. 27, 1993 [DE] Germany .............. 43 25 183.8

[51] Int. Cl.$^6$ ................................................. G01N 31/12
[52] U.S. Cl. .................. 436/137; 422/98; 204/424; 204/426; 338/34
[58] Field of Search .................. 422/94, 98; 338/34; 204/421, 424, 426, 431, 432; 436/137

[56] References Cited

U.S. PATENT DOCUMENTS

| | | | |
|---|---|---|---|
| 4,314,996 | 2/1982 | Sekido et al. | 422/98 |
| 4,789,454 | 12/1988 | Badwal et al. | 204/424 |
| 4,834,051 | 5/1989 | Tanaka et al. | 123/440 |
| 5,071,626 | 12/1991 | Tuller | 422/98 |

OTHER PUBLICATIONS

Nozaki et al. "Oxygen–Sensitive Resistivity of $La_2CuO_4$ at High Temperatures", *Japanese Journal of Applied Physics*, vol. 26, No. 11(Nov. 1987), pp.L1881–L1883.

*Primary Examiner*—Jeffrey Stucker
*Attorney, Agent, or Firm*—Evenson, McKeown, Edwards & Lenahan P.L.L.C.

[57] ABSTRACT

Cuprate mixed oxides having the general formula $Ln_2CuO_{4+y}$, in which Ln stands for at least lanthanum or a trivalent element from the group of rare earths with atomic numbers from 58 to 71, and the $O_2$ stoichiometric deviation y lies in the 0.001 to 0.1 range, are particularly suitable for use in oxygen sensors, for example in exhaust gas systems.

11 Claims, 2 Drawing Sheets

OXYGEN SENSOR BASED ON NON-DOPED CUPRATE

BACKGROUND OF THE INVENTION

The present invention relates to an oxygen sensor based on complex metal oxides of the general formula $$Ln_2CuO_{4+y}$$

wherein Ln is lanthanum or a lanthanide with the atomic number 58 to 71 and y is a value from 0.001 to 0.1, particularly an oxygen sensor which contains n- and/or p-semiconducting sensor materials, and to a process for the manufacturing of the sensor and to its use.

Gas detectors which contain sensor materials of the general formula $$A_{2-x}A'_xBO_{4-\delta}$$

are known (German Patent Document DE-23 34 044 C3). They are used, for example, in the form of the complex oxide $La_{1.4}Sr_{0.6}NiO_4$, not for detecting oxygen but for detecting oxidizable gases.

However, the cuprates which fall in the above formula are used only marginally in a non-doped form in the above-mentioned document and their capability for detecting oxidizable gases is not particularly distinctive.

SUMMARY OF THE INVENTION

It surprisingly was found that cuprates from the group of rare earths, even in a non-doped form, have an excellent oxygen sensing behavior if the oxygen stoichiometric deviation is set to a value of 4+y in the material.

It is therefore an object of the present invention to provide new oxygen sensors based on complex metal oxides of the general formula $$Ln_2CuO_{4+y}$$

which are particularly suitable for use in exhaust gas systems of motor vehicles, for example.

This object is achieved by means of an oxygen sensor based on complex metal oxides of the general formula $$Ln_2CuO_{4+y}$$

wherein Ln is lanthanum or a lanthanide with the atomic number 58 to 71, and y is a value from 0.001 to 0.1. In a preferred embodiment y is in the range of from 0.01 to 0.02. The sensor is preferably produced by applying the sensor materials to a metal oxide substrate. It is preferred that the substrate be non-conducting. The application of the sensor materials to the substrate is preferably by screen printing onto a metal oxide substrate, such as $Al_2O_3$.

In one embodiment according to the invention, the oxygen sensor may be arranged in a bridge circuit with one oxygen sensor with p-conducting sensor materials and one with n-conducting sensor materials. The sensors are connected to the same input for the input voltage in different bridge branches of the bridge circuit. In another embodiment, there is an arrangement in a bridge circuit of a series connection of one oxygen sensor with p-conducting sensor materials and another with n-conducting materials in one bridge branch, and in the other bridge branch, a series connection of two oxygen sensors of an n- and p- conducting material, respectively, being provided in such a manner that the oxygen sensor with the n-conducting sensor material in the one bridge branch is situated opposite the oxygen sensor with a p-conducting sensor material in the other bridge branch.

The oxygen stoichiometric deviation y is in the range from 0.001 to 0.1, preferably in the range of from 0.01 to 0.02.

The oxygen sensors according to the invention can be produced as follows:

The corresponding metal oxides, carbonates and/or oxycarbonates from the group of rare earths and copper are finely mixed by grinding with the addition of an organic solvent, such as cyclohexane. The ingredients are preferably mixed at the stoichiometric ratio. Grinding is preferably carried out in a suitable mill. The ground material is then caused to settle. The solvent is decanted and the ground material is dried. The powder is then calcined, in which case the calcining operation may be interrupted for a better mixing by another grinding. After the calcining, another grinding takes place, whereby a fine cuprate powder is obtained.

For setting the oxygen stoichiometric deviation of the thus obtained cuprate powders, they are glowed at high temperatures of preferably 850° to 1,100° C. in an oxygen-containing atmosphere, preferably pure oxygen.

By the addition of a paste matter and/or solvents, the thus obtained powder is processed to a paste, and the paste is applied by means of a thick film technique, for example, by screen printing, to a preferably non-conducting metal oxide substrate, such as $Al_2O_3$. The thus produced layer is dried and burnt, for example, by drying at temperatures above 100° C. and is subsequently fired at rising temperatures, optionally with a temperature profile in which rising temperatures alternate with constant temperatures. For obtaining the oxygen stoichiometric deviation, the firing is carried out in an oxygen-containing atmosphere, preferably pure oxygen. In this case, the firing temperatures may rise to approximately 1,200° C.

In this manner, a metal oxide substrate is obtained which is coated with the sensor materials and which, after the mounting of the usual feed and discharge lines, can be used directly as a sensor.

The oxygen sensors according to the invention are characterized by a low dependence on temperature and a high oxygen sensitivity at temperatures of preferably above 500° C. They exhibit fast adjusting kinetics. The measuring effect is not based on the change of a limit or surface resistance but on the change of the volume resistivity.

In contrast to the doped oxygen sensors of German Patent Application P 42 02 146.4-52, the non-doped cuprate materials according to the invention have the following advantages:

The oxygen sensor material may also be obtained without any targeted mixing-in of doping metals.

The temperature dependence is even less than in the case of doped cuprates. A linear dependency of the logarithm of the resistance on the logarithm of the partial oxygen pressure is obtained.

It is also an advantage for an arrangement to be provided in a bridge connection with one oxygen sensor with p-conducting sensor materials and one with n-conducting sensor materials, these being connected to the same input for the input voltage in different bridge branches of the bridge connection, and the measuring voltage being taken in the bridge diagonal. The remaining circuit elements of the bridge are ohmic resistances. This arrangement is particularly suitable for the circuiting of oxygen sensors which have different temperature sensitivities of the p-semiconducting and of the n-semiconducting sensor material.

Another possibility consists of using in each bridge branch two oxygen sensors with n-semiconducting and p-semiconducting sensor material in such a manner that, in one bridge branch, the oxygen sensor made of the n-conducting sensor material and, in the other bridge branch, the oxygen sensor made of the p-conducting sensor material are situated opposite one another, and vice versa.

BRIEF DESCRIPTION OF THE DRAWINGS

Other objects, advantages and applications of this invention will be made apparent by the following detailed description. The description makes reference to a preferred and illustrative embodiment of the invention presented in the accompanying drawings wherein.

DESCRIPTION OF THE PREFERRED EMBODIMENTS

Figure 2:
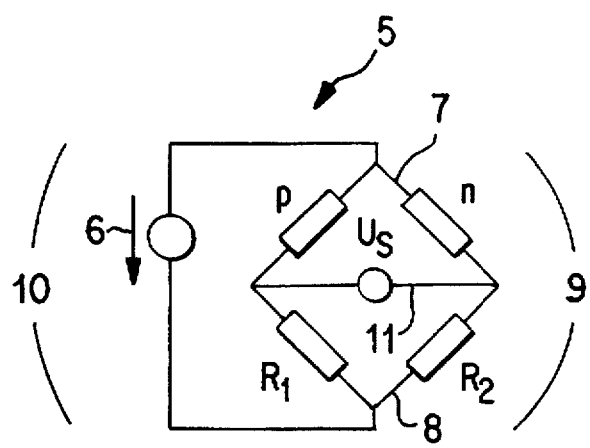
FIG. 2 is a schematic of a first electric arrangement of the oxygen sensors.

In FIG. 2, a bridge circuit is provided which, generally indicated by the reference number 5 and has an input current source 6, which is connected to the two inputs 7, 8 of the bridge. In one bridge branch 9, which extends between the inputs 7, 8 of the bridge circuit 5, the series connection of an oxygen sensor made of an n-conducting sensor material with an ohmic resistance of a given value $R_2$ is provided, and in the other bridge branch, the series connection of an ohmic resistance $R_1$ with an oxygen sensor of a p-conducting sensor material is provided, specifically such that, on the one hand, the resistances $R_1$ and $R_2$ are situated opposite one another in the two different branches, like the oxygen sensors with the p-semiconducting and n-semiconducting sensor material. The measuring voltage $U_s$ can be taken in the bridge diagonal 11.

Figure 3:
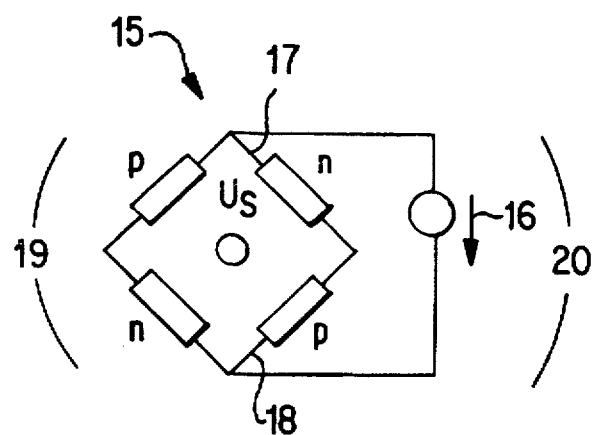
FIG. 3 is a schematic of a second possible arrangement of the oxygen sensors, each in a bridge connection.

In the alternative embodiment according to FIG. 3, the input voltage 16 in the bridge circuit 15, is connected between the inputs 17 and 18 of the bridge circuit 15. In each of the two branches 19, 20, the series connection of two oxygen sensors is arranged with, on the one hand, n-semiconducting and, on the other hand, with a p-semiconducting sensor material, specifically in such a manner that each oxygen sensor made of n-conducting sensor material in one bridge branch is situated opposite one with a p-conducting sensor material in the other branch, and vice versa. While the temperature sensitivity of the p- nd n-conducting sensor material is the same, this further development has the advantage that the highest temperature sensitivity is obtained while there is virtually no temperature dependence.

Additional examples will be described in the following.

EXAMPLE 1

Production of a Cuprate Powder according to the Formula $La_xCuO_{4+y}$

Powdery $La_2O_3$ is burnt out in an $Al_2O_3$-crucible at 830° C. for 4 hours. Then the furnace temperature is continuously cooled to approximately 200° C. The still hot $La_2O_3$ is taken out of the furnace and is mixed at the stoichiometric ratio of 1:0.24415 with CuO with the addition of cyclohexane in a grinding beaker for 1 hour. After a settling time of 30 minutes, the solvent is poured off. Then the ground material is dried in a drying stove at 60° C.

In the subsequent step, the powder mixture is calcined for 16 hours at 850° C. in air. By means of grinding, the calcined powder is changed to a median grain size of 5 μm. X-ray diffraction and powder particle size measurements are used for confirming the one-phase formation of $La_2CuO_{4+y}$ and of the powder grain size.

EXAMPLE 2

Production of a Cuprate Powder according to the Formula $La_2CuO_{4+y}$

Powdery, finely ground $La_2O_2CO_3$ (median grain size 1 μm) is mixed at a stoichiometric ratio of 1:0.2151 with finely ground CuO (median grain size 0.8 μm) with the addition of cyclohexane in a grinding beaker for 1 hour. After a settling time of 30 minutes, the solvent is poured off. Then the ground material is dried in a drying stove at 60° C.

In the subsequent step, the powder mixture is calcined for 16 hours at 850° C. in air. After a 1-hour intermediate grinding, the powder is calcined a second time for 16 hours at 850° C. By means of grinding, the twice-calcined powder is changed to a median grain size of 1.5 μm. X-ray diffraction and powder particle size measurements are used for confirming the one-phase formation of $La_2CuO_{4+y}$ and of the powder grain size.

EXAMPLE 3

Setting of the Oxygen Stoichiometric Deviation

The lanthanum cuprate powders produced according to the preparation direction 1.) and 2.) are glowed at 850° to 1,100° C. in pure oxygen. An analysis of oxygen content in the ceramics produced according to the preparation directions results in an oxygen overstoichiometry of 0.5%; that is, the compound $La_2CuO_{4.02}$ is present. The excess oxygen is preferably situated on interstitial sites.

Figure 1:
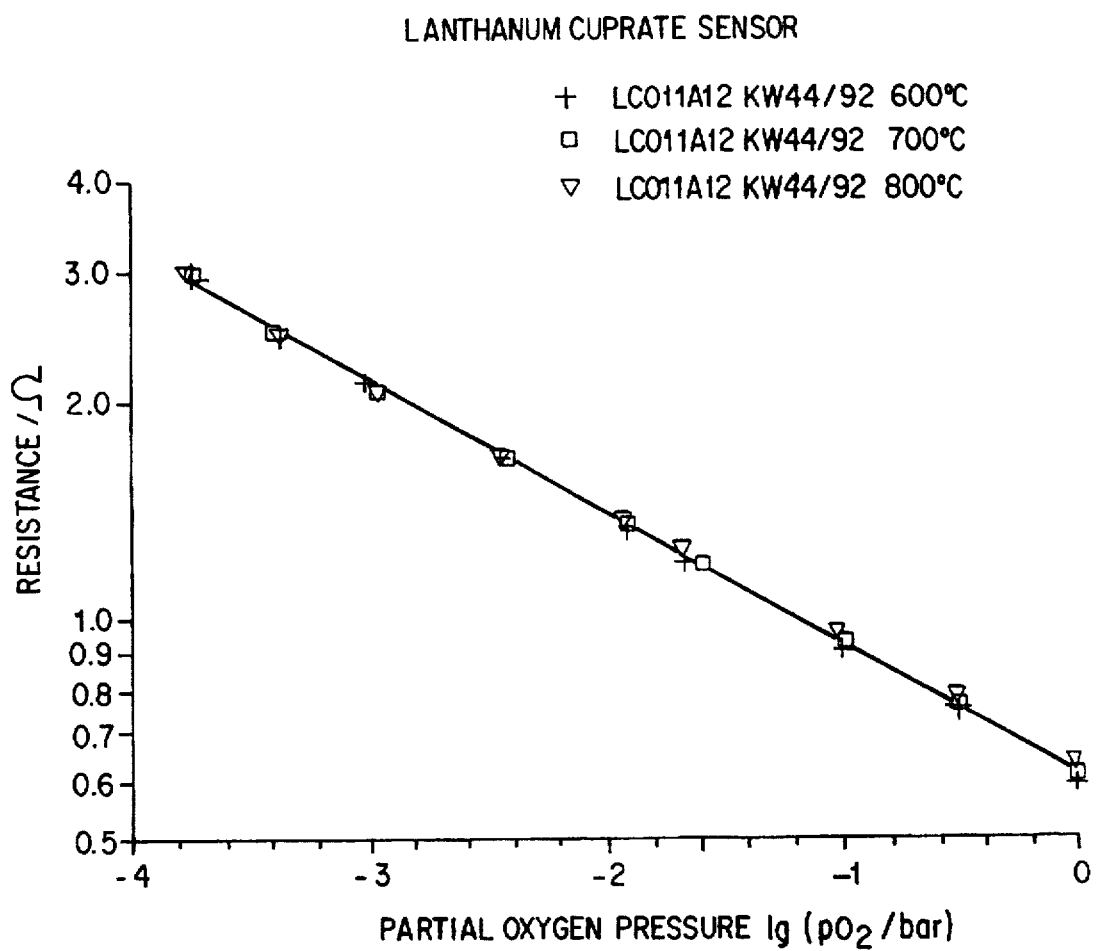
FIG. 1 is a curve showing the resistance of a lanthanum cuprate sensor plotted against the partial oxygen pressure.

The measuring of the electric resistance of a lanthanum cuprate sensor produced according to Examples 1 to 3 results in a dependence on partial oxygen pressure of the gas atmosphere, as illustrated in FIG. 1.

We claim:

1. A sensor material for an oxygen sensor to be used in an exhaust gas system, said sensor material comprising complex metal oxides of the formula $$Ln_2CuO_{4+y}$$

wherein Ln is lanthanum or a lanthanide having an atomic number of 58 to 71, and y is the oxygen stoichiometric deviation in the range from 0.001 to 0.1, wherein said complex metal oxides have a low dependence on temperature and a linear relationship of the logarithm of the resistance thereof to the logarithm of the oxygen partial pressure.

2. A sensor material according to claim 1, wherein y is in the range of from 0.01 to 0.02.

3. In combination, a sensor material according to claim 1, and a non-conducting metal oxide substrate.

4. The combination of claim 3, wherein said complex metal oxides are applied to the metal oxide substrate by screen printing.

5. A bridge circuit array of one oxygen sensor with p-conducting and one with n-conducting sensor materials, with these sensors being connected to the same input for the input voltage in different bridge branches of said bridge circuit, said sensors each comprising a sensor material according to claim 1.

6. A bridge circuit according to claim 5, comprising a bridge circuit array of one oxygen sensor with p-conducting and n-conducting sensor materials, with a series connection of two oxygen sensors of a p-conducting and an n-conducting sensor material being provided in one bridge branch, and with a series connection of two oxygen sensors of an n-conducting and p-conducting sensor material being provided in the other bridge branch in such a manner that the oxygen sensor with n-conducting sensor material in said one bridge branch is opposed by an oxygen sensor with p-conducting sensor material in the other bridge branch.

7. The combination of claim 4, wherein the metal oxide substrate is $Al_2O_3$.

8. A method of determining oxygen in exhaust systems comprising disposing an oxygen sensor which comprises the sensor material according to claim 1 in the exhaust system.

9. A method of producing an oxygen sensor which comprises a material according to claim 1, comprising finely mixing an oxide, carbonate, oxycarbonate, or mixtures thereof, of copper and a rare earth metal at the stoichiometric ratio, allowing the resulting powdered mixture to settle in an organic solvent, drying and calcining the mixture, and applying the powder in the form of a paste on a non-conducting metal oxide substrate and firing the same, and setting the oxygen stoichiometric deviation by sintering in an $O_2$-containing atmosphere.

10. A method according to claim 9, wherein calcining is carried out in two steps at temperatures from 800° to 1000° C. with an intermediate grinding step.

11. A method according to claim 9, wherein the firing is carried out at rising temperatures up to approximately 1200° C.

* * * * *